United States Patent [19]

Weber et al.

[11] Patent Number: 4,828,825

[45] Date of Patent: May 9, 1989

[54] INFRARED REFLECTING COMPOSITION FOR TOPICAL APPLICATION TO THE SKIN

[75] Inventors: Paul Weber; Oscar Hevia, both of Miami, Fla.

[73] Assignee: University of Miami, Coral Gables, Fla.

[21] Appl. No.: 907,508

[22] Filed: Sep. 15, 1986

[51] Int. Cl.$^4$ .......................... A61K 7/40; A61K 7/42; A61K 7/44

[52] U.S. Cl. ......................................... 424/59; 424/60

[58] Field of Search .................... 424/59, 60; 514/947, 514/949

[56] References Cited

U.S. PATENT DOCUMENTS

| | | | |
|---|---|---|---|
| 2,175,213 | 10/1939 | Parsons | 424/59 |
| 2,826,169 | 3/1958 | Le Veen | 424/59 X |
| 4,119,712 | 10/1978 | Goldner et al. | 424/63 |
| 4,486,405 | 12/1984 | Klein | 424/60 |
| 4,710,373 | 12/1987 | Nakamura et al. | 424/47 |

OTHER PUBLICATIONS

Derwent Abstract of Japanese Patent #49000450-A Accession No. 74-66798V/38 (01/05/74), Pola Chem. Kaufman, Chem. Abs; 1974, vol. 81, p. 111408f.
"Materials for Transparent Heat Mirror Coatings", G. Haacke, SPIE, vol. 324, Dec. 1982 pp. 10-15.
"Transparent Heat Insulating Coatings on a Polyester Film", Kiyoshi Chiba et al., SPIE, vol. 324, Dec. 1982, pp. 23-24.
"Noble-metal-based Transparent ingrared-reflectors; Preparation and Analysis of Thin Gold Films", G. B. Smith et al., SPIE, vol. 562, Apr. 1985, pp. 116-117.
"High Quality Transparent Heat Reflectors of Reactively Evaporated Indium Tin Oxide", I. Hamberg et al., SPIE vol. 324, Dec. (1982), pp. 31-32.
"Infrared Coatings for High Energy Laser Reflectors and Windows", M. Braunstein, SPIE vol. 140, Dec. (1978), pp. 85-94.
"Optical Coatings by Conveyorized Atmospheric Chemical Vapor Deposition (CVD)", N. Gralenski, SPIE vol. 324, Dec. (1982), pp. 44-51.
Appl. Phys. Lett., vol. 29, No. 8, Oct. 15, 1976, DuBow, Burk and Sites, p. 495.
"Preparation and Experimental Results", SPIE, vol. 324 Dec. (1982), pp. 59-60.
"Transparent Heat-Mirror films . . . ", J. Fan et al., Applied Physics Letters, vol. 25, No. 12, Dec. 15, 1974, pp. 693-695.

*Primary Examiner*—Dale R. Ore
*Attorney, Agent, or Firm*—Cushman, Darby & Cushman

[57] ABSTRACT

There is disclosed an infrared reflecting composition for topical application to the skin of a warm blooded animal comprising fine particles of an epidermally suitable substrate coated with at least one layer comprising an infrared reflecting amount of an infrared reflecting material. Also disclosed are methods of protecting the skin against infrared radiation by employing said composition or an infrared reflecting material alone.

22 Claims, 2 Drawing Sheets

A - UNCOATED SKIN
B - MICA FLAKES COATED WITH FLUORINE DOPED TIN OXIDE
C - UNCOATED MICA FLAKES

A - UNCOATED SKIN
B - GOLD COATED MICA
C - GOLD COATED MICA + AQUAPHOR

INFRARED REFLECTING COMPOSITION FOR TOPICAL APPLICATION TO THE SKIN

FIELD OF THE INVENTION

The present invention is directed to an infrared reflecting composition for topical application to the skin of a warm blooded animal. The composition can be used by sunbathers and those exposed to infrared radiation in their employment such as steel furnace operators, welders and the like to thereby limit exposure to infrared radiation.

BACKGROUND OF THE INVENTION

Radiant energy such as that emitted by the sun, welding arcs, light bulbs, etc. includes infrared radiation which is invisible to the naked eye and has a wavelength of at least 750 nm. Localized heating occuring as a result of exposure to infrared radiation can cause serious health problems. For example, it is known from animal studies that overexposure to both infrared and ultraviolet radiation can result in tumors of the skin. Additionally, infrared radiation is known to decrease skin elasticity leading to premature aging.

Topical applications for protection against radiant energy, especially from the sun have focused on protection against ultraviolet radiation. Ultraviolet absorbers have been used in such compositions and sold commercially as topical sunscreens (see, for example, U.S. Pat. No. 4,592,906).

Protection against infrared radiation has focused primarily on the employment of infrared absorbers such as those disclosed in U.S. Pat. No. 3,484,467. The infrared absorbers are incorporated into devices (e.g., sunglasses and safety lenses) which are sufficiently remote from the skin surface to insure that the heat absorbed by the infrared absorbers does not elevate skin temperature. For this reason, infrared absorbers have not been incorporated into compositions for the topical application to the skin.

Infrared reflectors are compounds which reflect infrared energy. Infrared reflecting films have been used to coat windows in high energy laser systems (see, "*Infrared Coatings For High Energy Laser Reflectors and Windows*", Morris Braunstein, SPIE, Vol. 140, Optical Coatings—Applications and Utilization II, pp. 85-94 (1978)). They have also been used to construct transparent heat mirrors for architectural glass coatings, light bulb envelopes, protective lenses, solar heat devices and the like. (See, "*Materials for Transparent Heat Mirror Coatings*", G. Haacke, SPIE, Vol. 324, Optical Coatings for Energy Efficiency and Solar Applications, pp. 10-15 (1982)). All of these infrared reflecting films are coated on relatively large substrates which are obviously unsuitable for topical compositions. Therefore, there is a need for a topical composition capable of protecting the skin against infrared radiation.

Applicants have discovered that an infrared reflecting composition for topical application to the skin can be prepared from infrared reflecting materials alone or by coating fine particles of an epidermally suitable substrate such as fine particles of mica or plastics with an infrared reflecting material. The resulting topical composition is easy to use and provides significant protection against infrared radiation from the sun, high energy arc lamps and the like.

It is therefore an object of the invention to provide an infrared reflecting composition for topical application to the skin.

It is another object of the invention to provide an infrared reflecting topical composition containing fine particles of an epidermally suitable substrate coated with an infrared reflecting material.

It is a further object of the invention to provide methods of protecting the skin of warm blooded animals against exposure to infrared radiation.

SUMMARY OF THE INVENTION

The present invention is directed to an infrared reflecting composition for topical application to the skin of warm-blooded animals comprising fine particles of an epidermally suitable substrate coated with at least one layer comprising an infrared reflecting effective amount of an infrared reflecting material. The present invention is also directed to methods of reflecting infrared radiation away from the skin by topically applying said compositions or an infrared reflecting material by itself to the skin.

The substrates employed in the present invention are, preferably, substantially transparent or reflect light in a manner which approximates the color tone of skin and include, by way of example, fine particles of mica or plastics such as, for example, polymethacrylate, polyethylene terephthalate and the like. The particle size of the substrate should be sufficiently small so as to enable the composition to be easily and evenly applied to the skin. The preferred particle size of the substrate is within the range of from about 20 to about 500 microns. Mica is the preferred substrate for use in the present invention.

The fine particles of the substrate are coated with at least one layer comprising an infrared reflecting amount of an infrared reflecting material. The infrared reflecting materials are preferably substantially transparent or reflect light in a manner which approximates the color tone of skin. Under these circumstances, the present composition is substantially invisible or at least barely noticeable when applied to the skin. The infrared reflecting materials particularly suited for the present invention include metals and semiconductor materials such as doped tin oxide, doped indium oxide and cadmium orthostannate wherein the dopants are preferably selected from fluorine, phosphorous and tin. Such dopants are known to enhance the infrared reflecting properties of the semiconductor material. Of the semi-conductor type infrared reflectors, fluorine doped tin oxide is particularly preferred. In the present invention, the dopant is employed in an amount sufficient to enhance reflectance, typically no more than about 1 mol % based on the total amount of the infrared reflecting material.

The semiconductor infrared reflecting material is coated on the substrate to a thickness sufficient to insure a suitable degree of infrared reflectance. For most applications including protection from infrared radiation generated by the sun, it is preferred to coat the substrate with the semiconductor material to a thickness in the range of from about 3,000 to 4,000 Å.

The metals which are employed as infrared reflectors in the present invention include the noble metals (e.g., gold, silver, platinum, etc.), copper and aluminum. In a preferred embodiment of the invention, the metal may be coated on each of its sides with a dielectric material such as titanium dioxide or zinc sulfide or combinations thereof to obtain an infrared reflecting composition which has improved visible transparency and enhanced infrared reflectivity.

The thickness of the metal containing infrared reflecting coating is preferably in the range of from about 100 to about 300 Å.

The infrared reflecting compositions may be produced by applying a coating of the infrared reflecting material on the fine particles of the substrate by conventional methods such as chemical vapor deposition, evaporation, sputtering, spray pyrolysis and the like. Alternatively, the substrate may be coated as a sheet and then the coated sheet ground into fine particles.

The coated substrates may be applied to those areas of the skin which are exposed to infrared radiation. The coated substrates may be added to dermatologically suitable carriers if desired. Suitable carriers include SD alcohol, lanolin, glyceryl stearate, cocoa butter, sorbitan sesquioleate, propylene glycol, mineral oil, isopropyl myristate, petrolatum and Aquaphor sold by Beiersdorf (a mixture of petrolatum, mineral oil, mineral wax, wool wax and alcohol) and mixtures thereof. The amount of the carrier need only be sufficient to provide a uniform dispersion of the active ingredient when applied to the skin and to insure coverage of the skin with the infrared reflecting material, typically from about 85 to about 95 percent by weight based on the overall weight of the composition.

The composition of the present invention may contain a variety of additives including, for example, ultraviolet absorbers, stabilizers, fragrances, and the like.

Ultraviolet absorbers of the type described in U.S. Pat. No. 4,592,906 incorporated herein by reference may be used to produce a composition giving protection against both ultraviolet and infrared radiation.

The following examples are for illustrative purposes only and are not meant to limit the invention as set forth in the claims forming a part of the application.

EXAMPLE 1

Preparation of Doped Tin Oxide Coated Mica

A chemical vapor deposition apparatus including a resistance-heated Kanthal wire furnace (Lindberg, Model M-200) containing a 50 mm×1.8 mm reaction chamber made of fused silica is loaded with a sheet of mica. Dibutyltin diacetate and trichlorotrifluoro ethane (Freon 113 sold by DuPont Canada, Inc.) as a dopant are maintained at temperatures of 100° C. and 0° C., respectively in the presence of bubbled nitrogen gas in order to maintain the desired vapor pressure for each compound.

Prior to deposition, the substrate is preheated for about five minutes under a nitrogen gas flow. Tin oxide is coated on the mica sheet by exposing the mica sheet to approximate flow rates respectively as follows: 400 m./min nitrogen carrier gas, 550 ml/min oxygen, 1.14 liter/min nitrogen through the dibutyltin diacetate reactor and 25 to 280 ml/min of nitrogen through the Freon 113 reactor.

Figure 1:
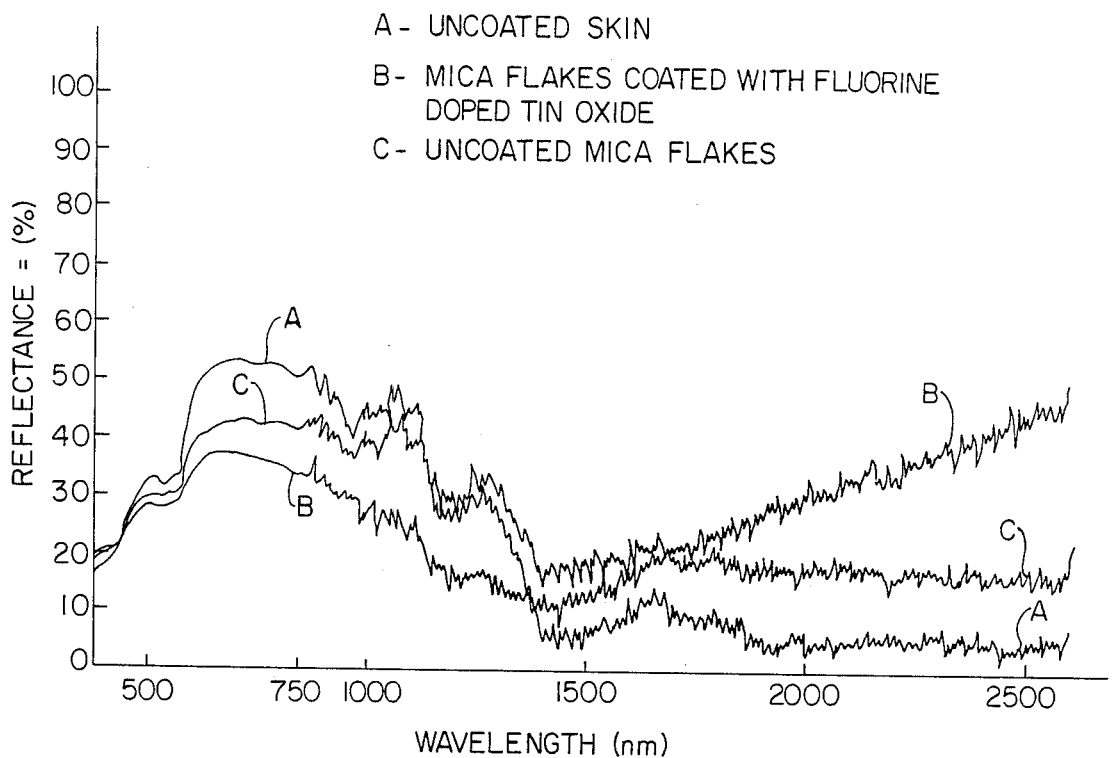
FIG. 1 is a graph showing the degree of reflectance of infrared radiation of a composition of the present invention containing fluorine doped tin oxide on mica as compared with the reflectance of the uncoated substrate and unprotected human skin.

After deposition, the sheet of mica was cut into fine particles of mica (about 500 microns$^2$) and then applied to human skin and tested for infrared reflectance by a Perken Elmer Lambda 9 UV-Visible NIR-Spectrophotometer and the results are shown in FIG. 1.

As shown in FIG. 1, the coated mica particles exhibited significantly greater reflection of infrared radiation than uncoated mica and unprotected skin.

EXAMPLE 2

Preparation of A Sandwich Film of Titanium Dioxide (Dielectric) and Gold

A sheet of mica is ultrasonically cleaned in a heated decontamination solution (DECONTAM sold by Electronic Space Products, Inc., Los Angeles, Calif.), rinsed in deionized water and blown dry in nitrogen gas.

A TiO$_2$ target is presputtered at 1.6 W/cm$^2$ in an Argon-oxygen mixture (10 vol % Oxygen) for 15 minutes, then in Argon for 15 minutes. The flow rates of the Argon-Oxygen mixture and Argon are kept at about 74 cm$^3$/min. The sputtering pressure is $7-10\times10-3$ Torr.

A TiO$_2$ film having a thickness of about 180 Å is deposited on the sheet of mica by sputtering at 0.8 W/cm$^2$ for 7.5 minutes in Argon at a flow rate of about 74 cm$^3$/min at the same sputtering pressure employed above.

A film of gold approximately 180 Å thick is deposited by sputtering at 0.4 W/cm$^2$ for 35 seconds in Argon and the same flow rate and sputtering pressure described above for depositing the TiO$_2$ film.

Another TiO$_2$ film is deposited on the gold film in the same manner as described above for the deposition of the initial TiO$_2$ film. The resulting product reflects at least about 75% infrared radiation in the near IR region (750-1000 nm) and approaches 100% reflectance at about 3,000 nanometers.

EXAMPLE 3

Gold Coated Mica

A piece of gold wire 19.2 mm long and 0.2 mm wide weighing about 8 mg was twisted around a tungsten filament secured within a Denton Vacuum Machine Model No. DV-502. The filament was connected to two electrodes and a petri dish containing fine particles of mica (e.g., 20 to 500 microns) was placed about 5 to 7.5 cm below the filament.

The gold wire was heated and subsequently evaporated onto the mica particles at a vacuum pressure of $10^{-5}$ Torr at 20 amps and 45 volts for 3 seconds.

The gold coated fine particles of mica were combined with Aquaphor at a weight ratio of about 1:10 (10 mg gold coated mica:100 mg Aquaphor) and mixed until the gold coated mica was uniformly dispersed in the Aquaphor to produce an infrared reflecting composition for topical application. The composition was applied to human skin and tested for infrared reflectance in the same manner as in Example 1. The results are shown in FIG. 2.

The experiment is repeated except that the gold coated mica was not combined with Aquaphor. The gold coated mica alone was applied to human skin and tested for infrared reflectance in the same manner as Example 1. The results are shown in FIG. 2.

Figure 2:
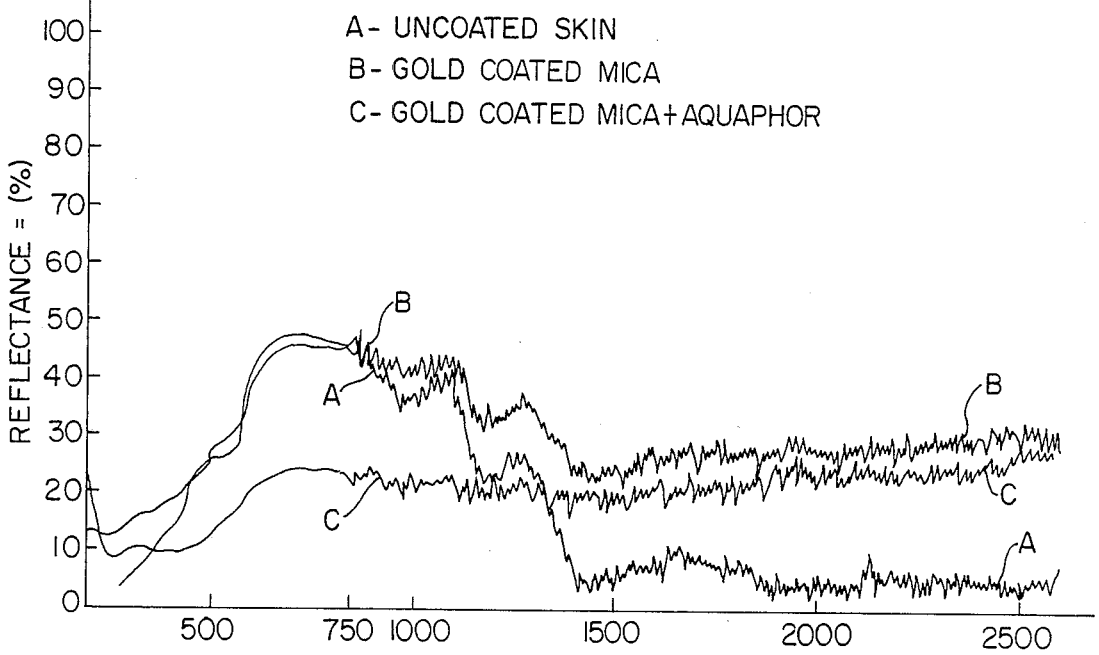
FIG. 2 is a graph showing the degree of infrared reflectance of gold powder and a composition of gold and a dermatologically acceptable carrier as compared with unprotected human skin.

As shown in FIG. 2, the gold coated mica alone and the gold coated mica combined with Aquaphor exhibited significantly greater infrared reflectance than unprotected skin.

EXAMPLE 4

Preparation of Doped Tin Oxide Crystals

Figure 3:
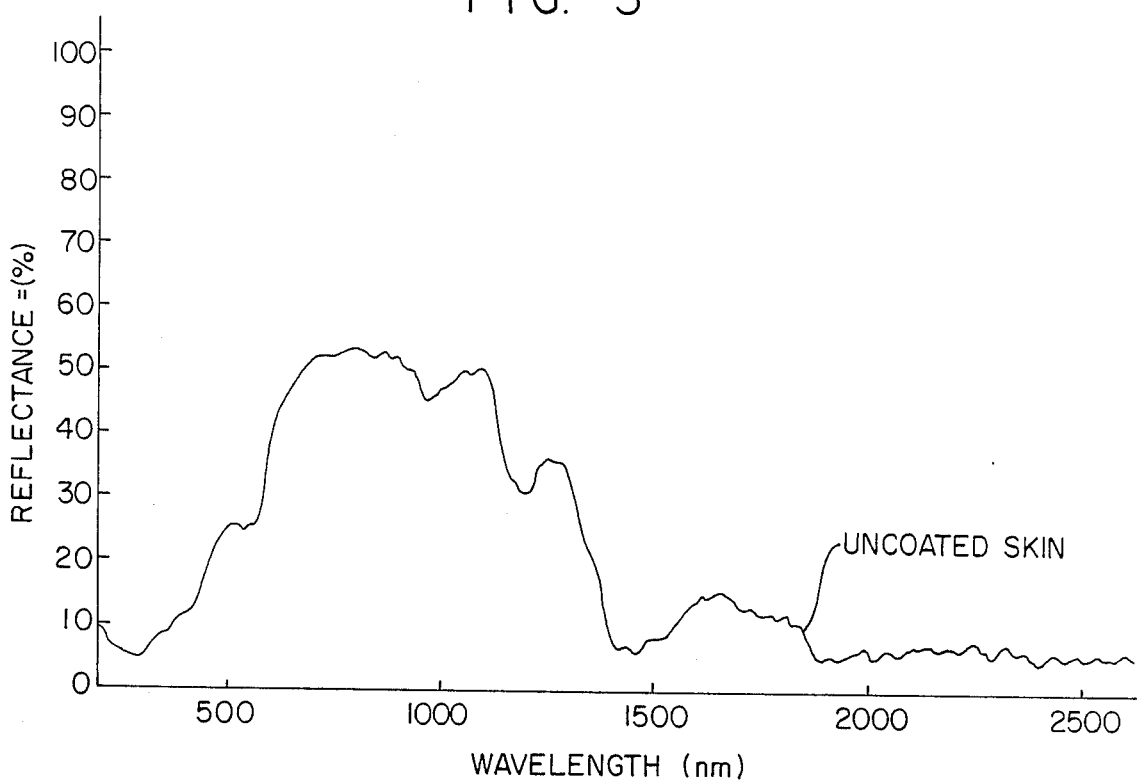
FIG. 3 is a graph showing the degree of infrared reflectance of unprotected human skin.
Figure 4:
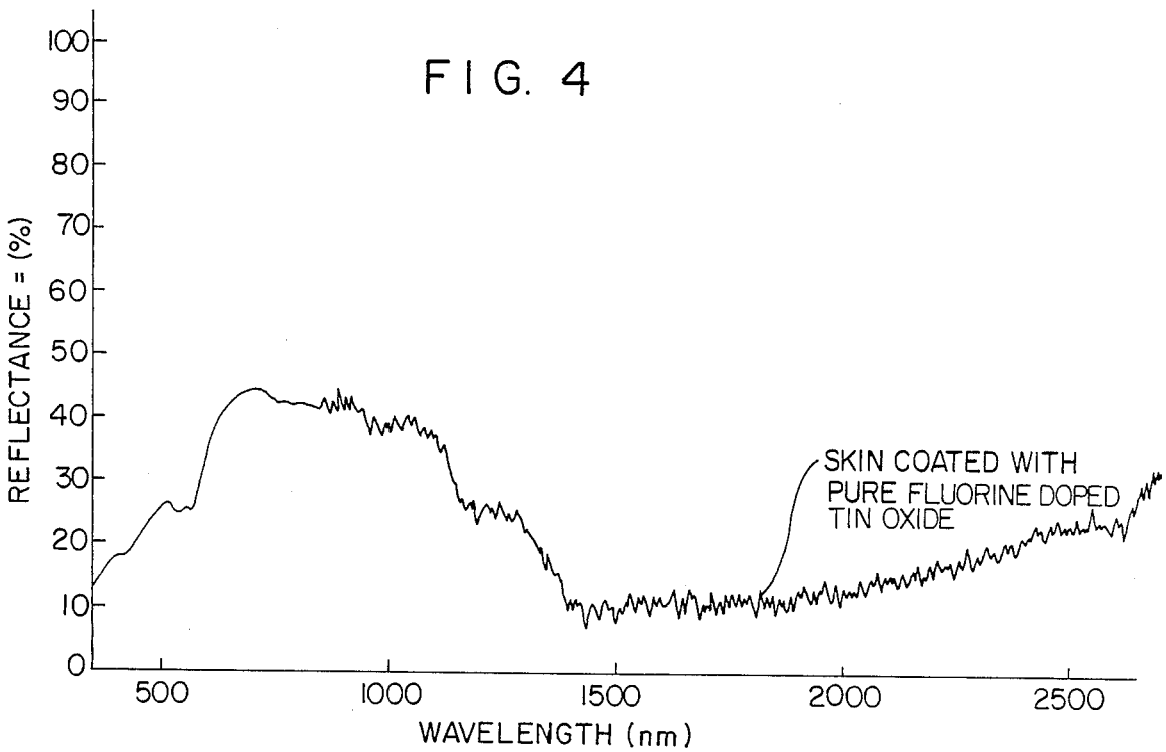
FIG. 4 is a graph showing the degree of infrared reflectance of human skin coated with fluorine doped tin oxide alone.

Fluorine doped tin oxide is coated on a sheet of mica employing the same method described in Example 1. The doped tin oxide coating was separated from the mica sheet using a fine knife to obtain fine particles of doped tin oxide which were applied to the skin as a topical composition. The degree of infrared reflectance of the coated skin as shown in FIG. 4 is significantly greater than the infrared reflectance of uncoated skin as shown in FIG. 3.

We claim:

1. An infrared reflecting composition for topical application to the skin of a warm blooded animal comprising a dermatologically acceptable carrier having dispersed therein fine particles of mica coated with at least one layer comprising an infrared reflecting material selected from doped tin-oxide, doped indium oxide, cadmium orthostannatem noble metals, copper aluminum, and combinations thereof.

2. The composition of claim 1 wherein said composition further comprises at least one composite comprising a layer of said infrared reflecting metal sandwiched between a top and bottom layer of a dielectric material, wherein the bottom layer of the bottommost composite is superimposed over the substrate.

3. The composition of claim 2 wherein the dielectric material is selected from titanium dioxide and zinc sulfide.

4. The composition of claim 3 wherein the metal is gold.

5. The composition of claim 1 wherein the infrared reflecting material is substantially transparent or reflects light in a manner which approximates the color tone of skin.

6. The composition of claim 1 wherein the dopant is selected from fluorine, phosphorous and tin.

7. The composition of claim 6 wherein the noble metal is gold.

8. The composition of claim 1 wherein the mica has a particle size in the range of from about 20 to about 500 microns.

9. The composition of claim 1 wherein the infrared reflecting material is selected from noble metals, copper and aluminum and the thickness of the infrared reflecting layer is in the range from about 100 to about 300 Å.

10. The composition of claim 1 wherein the infrared reflecting material is selected from doped tin oxide, doped indium oxide and cadmium stannate and the thickness of the infrared reflecting layer is in the range of from about 3000 to about 4000 Å.

11. The composition of claim 1 further comprising an ultraviolet absorber.

12. An infrared reflecting composition for topical application to the skin of a warm blooded animal comprising a dermatologically acceptable carrier having dispersed therein fine particles of a substrate selected form mica, polyethylene terephthalate and polymethacrylate coated with at least one layer comprising a infrared reflecting material selected from doped tin-oxide, doped indium oxide, cadmium orthostannate, noble metals, copper, aluminum, and combinations thereof.

13. The composition of claim 12 wherein the substrate has a particle size in the range of from about 20 to about 500 microns.

14. The composition of claim 12 wherein the infrared reflecting material is a metal and the thickness of the infrared reflecting layer is in the range of from about 100 to about 300 Å.

15. The composition of claim 12 wherein the infrared reflecting material is a semiconductor and the thickness of the infrared reflecting layer is in the range of from about 3000 to about 4000 Å.

16. The composition of claim 12 further comprising an ultraviolet absorber.

17. An infrared reflecting composition for topical application to the skin of a warm blooded aimal comprising a dermatologically acceptable carrier having dispersed therein fine particles of a substrate having a particle size in the range of about 20 to about 500 microns selected form mica, polyethylene terephthalate and polymethacrylate coated with at least one layer comprising an infrared reflecting material selected from doped tin-oxide, doped indium oxide, cadmium orthostannate, noble metals, copper, aluminum, and combinations thereof wherein the thickness of the infrared reflecting metal layer is in the range of from about 100 to about 300 Å, and the thickness of the infrared reflecting semiconductor layer is in the range of from about 3000 to about 4000 Å.

18. A method of reflecting infrared radiation away from the skin of a warm blooded animal comprising topically applying to the skin an infrared reflecting amount of an infrared reflecting composition comprising an infrared reflecting material selected from doped tin oxide, doped indium oxide, cadmium orthostannate, noble metals, copper, aluminum, and combinations thereof or fine particles of an epidermally suitable substrate selected form mica, polyethylene terephthalate and polymethacrylate coated with at least one layer comprising at least one of said infrared reflecting materials.

19. The method of claim 18 wherein the infrared reflecting composition further comprises a dermatologically acceptable carrier.

20. The method of claim 18 further comprising topically applying an ultraviolet absorber alone or as part of said composition to thereby protect the skin against ultraviolet radiation.

21. A method of reflecting infrared radiation away from the skin of a warm blooded animal comprising topically applying to the skin an infrared reflecting amount of an infrared reflecting composition according to claim 12.

22. A method of reflecting infrared radiation away from the skin of a warm blooded animal comprising topically applying to the skin an infrared reflecting amount of an infrared reflecting composition according to claim 17.

* * * * *